(12) United States Patent
Krossing et al.

(10) Patent No.: US 7,683,194 B2
(45) Date of Patent: Mar. 23, 2010

(54) METHOD FOR THE PRODUCTION OF SALTS OF WEAKLY COORDINATING ANIONS, SALTS THEREOF AND USE THEREOF

(75) Inventors: Ingo Krossing, Freiburg (DE); Marcin Gonsior, Elblag (PL); Lutz Muller, Feiburg (DE)

(73) Assignee: Universitat Freiburg, Freiburg (DE)

( * ) Notice: Subject to any disclaimer, the term of this patent is extended or adjusted under 35 U.S.C. 154(b) by 588 days.

(21) Appl. No.: 10/580,974

(22) PCT Filed: Oct. 28, 2004

(86) PCT No.: PCT/EP2004/012220

§ 371 (c)(1), (2), (4) Date: Jun. 12, 2007

(87) PCT Pub. No.: WO2005/054254

PCT Pub. Date: Jun. 16, 2005

(65) Prior Publication Data

US 2008/0033195 A1    Feb. 7, 2008

(30) Foreign Application Priority Data

Dec. 4, 2003 (DE) ............................. 103 56 768

(51) Int. Cl.
*C07F 5/02* (2006.01)
*C07F 5/06* (2006.01)
*C07F 19/00* (2006.01)
*C07F 9/02* (2006.01)

(52) U.S. Cl. .............. 556/6; 556/7; 556/14; 556/27; 556/28; 556/30; 556/182; 568/6; 568/14

(58) Field of Classification Search ............... 556/6, 556/7, 27, 28, 30, 182; 568/6, 14
See application file for complete search history.

(56) References Cited

FOREIGN PATENT DOCUMENTS

WO    WO 00/53611    * 9/2000

OTHER PUBLICATIONS

Gonsior wt al., Chem. Eur. J., vol. 8, No. 19, pp. 4475-4492 (2002).*
Barbarich et al., Organometallics, vol. 15, No. 18, pp. 3776-3778 (1996).*
Bihlmeir et al., Chem. Eur. J., vol. 10, No. 20, pp. 5041-5051 (2004).*

* cited by examiner

*Primary Examiner*—Porfirio Nazario Gonzalez
(74) *Attorney, Agent, or Firm*—Renner, Otto, Boisselle & Sklar, LLP

(57) ABSTRACT

The invention relates to a method for the production of salts of weakly coordinating anions of the type according to the following formula (1), (2) or (3): $M[F-X(OR\ F)_m]_z$ (1), $M[(^FRO)_mX-F-X(OR^F)_m]_z$ (2), $M[(^FRO)_mX-F-X(OR^F)_n-F-X(OR^F)_m]_z$ (3), these salts of weakly coordinating anions and use thereof.

19 Claims, No Drawings

METHOD FOR THE PRODUCTION OF SALTS OF WEAKLY COORDINATING ANIONS, SALTS THEREOF AND USE THEREOF

The invention relates to a method for the production of salts of weakly coordinating anions of the type corresponding to the following formula (1), (2) or (3):

  (1)

  (2)

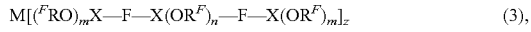  (3), salts of such weakly coordinating anions and use thereof.

Weakly coordinating anions represent a special field that is currently the subject of much investigation, in particular as directed at industry and basic applications.

Examples of applications include use as counterions for cationic catalysts so as to strengthen the catalytic activity thereof, use as electrolyte salts in batteries, use as components in ionic fluids or use as conducting salts in electrochemistry. In particular, when such weakly coordinating anions have fluorine-rich organic groups, they are also suitable for the preparation of catalysts, which can be regenerated by fluorous phase extraction.

Conventional, well-known weakly coordinating anions are either disadvantageous in terms of properties, having, for example, insufficient thermal and/or hydrolytic stability, insufficient conductivity or excessive coordinative strength, or are only available in small quantities. Thus, one of the best-known anion classes, halogenated carboranates, are available only in small quantities (gram range) after multi-stage synthesis. Furthermore, highly explosive $C_6F_5Li$ is used as intermediate in the synthesis of commonly used $B(C_6F_5)_4^-$ anions.

Weakly coordinating anions of the $Al(OR)_4^-$ (OR=polyfluorinated aliphatic alkoxide) type are known from WO 00/53611.

Over the course of further experiments in this field it was discovered that an anion of the type $[(^FRO)_3Al—F—Al(OR^F)_3]^-$ ($^FRO$=fluorinated alkoxide) is formed in the presence of extremely reactive cations (see M. Gonsior, I. Krossing, L. Müller, I. Raabe, M. Jansen, L. van Wüllen, *Chem. Eur. J.* 2002, 8, 4475; I. Krossing *Dalton Trans.* 2002, 500). But up to now, this fluoride-bridged anion $[(^FRO)_3Al—F—Al(OR^F)_3]^-$ could only be obtained as a decomposition product, for example, in the reaction of $P_2I_4$ with $Ag[Al(OR^F)_4]$.

Accordingly, there is currently no known effective route to such salts of weakly coordinating anions, which are of interest for industrial applications. An analysis of the parameters of the aforementioned anions $[(^FRO)_3Al—F—Al(OR^F)_3]^-$ as well as quantum chemical calculations do in fact demonstrate that, to date, this is the best of the known types of weakly coordinated anion. Because it has an elevated number of peripheral fluorine atoms [for example 54 fluorine atoms for $^FR=(F_3C)_3C$], the corresponding fluoride-bridged $\{[(F_3C)_3CO]_3Al—F—Al[OC(CF_3)_3]_3\}^-$ anion is more weakly coordinating and more stable against ligand abstraction than the homoleptic $\{Al[OC(CF_3)_3]_4\}^-$ anion with only 36 peripheral fluorine atoms.

It is therefore the object of the invention to provide a method for preparing of salts of weakly coordinating anions, whereby such salts can be produced easily, at high yields and on any scale.

This problem is solved by way of the embodiments characterized by the claims.

In particular, a method for preparing salts of weakly coordinating anions of the type corresponding to one of the following formulas (1), (2) or (3) is provided:

  (1)

  (2)

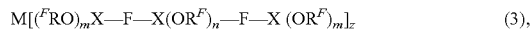  (3), wherein, in a first step, an organyl compound of an element $XR_m$ is reacted with a partially or completely fluorinated alcohol $^FROH$ in an organic, aprotic solvent and then, in a second step, the resulting alkoxy compound of the element $X(OR^F)_m$ is reacted with a suitable fluoride salt $M_yY_z$ so as to abstract a fluoride ion, if necessary under $XF_m$-catalysis, wherein:

X is selected from the group consisting of B, Al, Ga, In, P, As and Sb,
M is a monovalent or bivalent cation,
m is 3 or 5 and
n is 2, if m is 3, and/or
n is 4, if m is 5,
y is 1 or 2, provided that, if y is 1, Y is a monovalent anion, and/or if y is 2, Y is a bivalent anion, and
z is 1 or 2, provided that, if z is 1, M is a monovalent cation, and/or if z is 2, M is a bivalent cation.

A preferred embodiment of the invention provides a method for preparing salts of weakly coordinating anions corresponding to one of the following formulas (1'), (2'), or (3'):

  (1')

  (2')

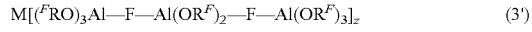  (3')

wherein, in the first step an aluminum triorganyl compound $AlR_3$ is reacted with a partially or completely fluorinated alcohol $^FROH$ in an organic, aprotic solvent, and then, in the second step the resulting aluminum trialkoxy compound $Al(OR^F)_3$ is reacted with a tetrafluoroborate salt $M(BF_4)z$, if necessary under $BF_3$-catalysis.

In the method of the invention, the alkoxy compound of the element $X(OR^F)_m$ which is preferably an aluminum trialkoxy compound $Al(OR^F)_3$, may be reacted in the second step with a suitable fluoride salt $M_yY_z$, which is preferably a tetrafluoroborate salt $M(BF_4)z$, so as to abstract a fluoride ion, at a ratio of 1:1, if z is 1, or at a ratio of 2:1, if z is 1 or 2, or at a ratio of 4:1, if z is 2.

If the reaction ratio as mentioned above is 1:1, in the case where z is 1, or if it is 2:1 in the case where z is 2, the method according to the invention forms salts of weakly coordinating anions corresponding to formula (1) or formula (1').

If the reaction ratio as mentioned above is 2:1, in the case where z is 1, or 4:1, in the case where z is 2, the method according to the invention forms salts of weakly coordinating anions corresponding to formulas (2), (3), (2') or (3') as a function of the reaction conditions selected.

In the method according to the invention, there are no particular restrictions on the organic, aprotic solvent used, as long as it is non-coordinating and has no donor properties. Generally, in the method according to the invention the solvent is chosen from the group consisting of alkanes, aromatics and halogenated aromatics. Preferably, the solvent is selected from the group consisting of pentane, hexane, heptane, octane, benzene, toluene, cresol, chlorobenzene and trichlorobenzene.

In the first step of the method of the invention, an organyl compound of an element $XR_m$, and in particular an aluminum triorganyl compound $AlR_3$, is reacted with a partially or completely fluorinated alcohol $^FROH$ in the organic, aprotic solvent. The radical R of the organyl compound of the element is preferably selected from the group consisting of hydrogen, methyl, ethyl, n-propyl, i-propyl, n-butyl, i-butyl, t-butyl, phenyl and tolyl.

The partially or completely fluorinated alcohol $^FROH$ used in the method of the invention as described above preferably has an $^FR$ radical, which is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups. Among these, perfluorinated groups are particularly preferred.

The following partially or completely fluorinated alcohols $^FROH$ may be cited: $HO-C(CF_3)_3$, $HO-C(R^1)(CF_3)_2$, $HO-C(R^1)(R^2)(CF_3)$ and $HO-C(R^1)(R^2)(R^3)$, wherein $R^1$, $R^2$ and $R^3$, may be, independently of each other, hydrogen, linear or branched, partially or completely fluorinated $C_1$ to $C_{10}$ alkyl groups, partially or completely fluorinated $C_6$ to $C_{20}$ aryl groups and partially or completely fluorinated $C_3$ to $C_{10}$ cycloalkyl groups, provided that in the case of $HO-C(R^1)(R^2)(R^3)$, at least one of $R^1$, $R^2$ and $R^3$ is a partially or completely fluorinated radical, as described above. Particularly preferred is $HO-C(CF_3)_3$ or an alcohol $HO-C(R^1)(R^2)(R^3)$ as mentioned above, which has at least one $R^1$, $R^2$ or $R^3$ radical, which is a perfluorinated $C_1$ to $C_{10}$ alkyl group, and in particular a $C_1$ to $C_6$ alkyl group, such as, for example, $-C_6F_{13}$. The latter are particularly suited for subsequent fluorous phase extraction of the corresponding salts, which result from the method of the invention.

In the second step of the method, a suitable fluoride salt $M_yY_z$ is used for abstraction of a fluoride ion.

Thus, Y is normally selected from the group consisting of $BF_4^-$, $PF_6^-$, $SiF_6^{2-}$, $SbF_4^-$, $SbF_6^-$, $AsF_4^-$, $AsF_6^-$, $SnF_5^-$, $SnF_6^-$, $GeF_5^-$ and $GeF_6^{2-}$. Preferably, in the method of the invention, a tetrafluoroborate salt $M(BF_4)_z$ is used as the suitable fluoride salt for the abstraction of the fluoride ion, wherein if z is 1, M is selected from the group consisting of alkali metal ions, $In^+$, $Ti^+$, $Ag^+$, $Cu^+$, $NR'_4^+$ and $PR'_4^+$, wherein R', is independently in each case hydrogen, a linear or branched $C_1$ to $C_{20}$-alkyl radical or substituted or unsubstituted aryl radical, such as, in particular, phenyl or tolyl, and imidazolium, or if z is 2, M is selected from the group of transition metals preferably consisting of $Ni^{2+}$, $Cu^{2+}$, $Zn^{2+}$, $Pd^{2+}$, $Rh^{2+}$, and $Pt^{2+}$,.

In a particularly preferred embodiment of the present invention:

i) in the first step, the aluminum triorganyl compound $AlMe_3$ is reacted with the partially or completely fluorinated alcohol $^FROH$ in pentane, at a ratio of 1:3, and then, in the second step, the resulting aluminum trialkoxy compound $Al(OR^F)_3$ is reacted with a tetrafluoroborate salt $M(BF_4)z$, at a ratio of 1:1, if z is 1, or at a ratio of 2:1, if z is 2, which yields a compound corresponding to formula (1') above;

ii) in the first step, the aluminum triorganyl compound $AlMe_3$ is reacted with the partially or completely fluorinated alcohol $^FROH$ in pentane, at a ratio of 1:3, and then, in the second step, the resulting aluminum trialkoxy compound $Al(OR^F)_3$ is reacted with a tetrafluoroborate salt $M(BF_4)z$, at a ratio of 2:1, if z is 1, or at a ratio of 4:1, if z is 2, which yields a compound corresponding to formula (2') above; or iii) in the first step, the aluminum triorganyl compound $AlMe_3$ is reacted with the partially or completely fluorinated alcohol $^FROH$ in heptane at a ratio of 1:3, and then, in the second step, the resulting aluminum trialkoxy compound $Al(OR^F)_3$ is reacted with a tetrafluoroborate salt $M(BF_4)z$, at a ratio of 2:1, if z is 1, or at a ratio of 4:1, if z is 2, which yields a compound corresponding to formula (3') above.

In the alternative embodiments i) to iii) of the method of the invention, it is particularly preferred that, in the first step, a completely fluorinated alcohol $^FROH$ is used, wherein $R^F$ is $(F_3C)_3C$.

Moreover, in the alternative embodiments described above, in the second step, a tetrafluoroborate salt $M(BF_4)z$ is preferably used, wherein M is $Ag^+$ or $NBu_4^+$.

The invention also relates to other salts of a weakly coordinating anion, represented by formula (3):

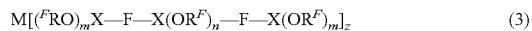

$$M[(^FRO)_mX-F-X(OR^F)_n-F-X(OR^F)_m]_z \quad (3)$$

wherein X is selected from the group consisting of B, Al, Ga, In, P, As and Sb,

M is a monovalent or bivalent cation, m is 3 or 5 and n is 2, if m is 3, and/or n is 4, if m is 5, z is 1 or 2, provided that, if z is 1, M is a monovalent anion, and/or if z is 2, M is a bivalent anion, and wherein, if z is 1, M is selected from the group consisting of alkali metal ions, $In^+$, $Ti^+$, $Ag^+$, $Cu^+$, $NR'_4^+$, $PR'_4^+$, wherein R' is, independently in each case, hydrogen, a linear or branched $C_1$ to $C_{20}$-alkyl radical or substituted or unsubstituted aryl radical, and in particular phenyl or tolyl, and imidazolium, or, if z is 2, M is selected from the group of transition metals preferably consisting of $Ni^{2+}$, $Cu^{2+}$, $Zn^{2+}$, $Pd^{2+}$, $Rh^{2+}$, and $Pt^{2+}$, and $R^F$ is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups, perfluorinated groups being particularly preferred.

In a preferred embodiment, the present invention relates to salts of a weakly coordinating anion corresponding to formula (3'):

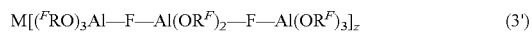

$$M[(^FRO)_3Al-F-Al(OR^F)_2-F-Al(OR^F)_3]_z \quad (3')$$

wherein z, M and $R^F$ are as defined above.

In a particularly preferred embodiment of the salts with formulas (3) or (3') according to the invention, M is $Ag^+$ or $NBu_4^+$ and $R^F$ is $(F_3C)_3C$.

The salts of a weakly coordinating anions according to the invention have a broad field of industrial application. They may find application as adjuvants in ionic fluids or in lithium ion batteries, in electrochemistry as inert conducting salts such as in lithium ion electrolytes, or in homogeneous catalyses such as olefin polymerization, metallocene catalysis, lithium catalysis of organic reactions and other organic syntheses. Accordingly, a further object of the present invention relates to the use of these types of salts, particularly in ionic fluids, in lithium ion batteries, as conducting salts in electrochemistry or in homogeneous catalysis.

The anions of the invention are advantageous in terms of stability, weaker coordination strength and synthetic availability, as compared to conventional anions.

In addition, the invention relates to the alkoxy compounds of elements obtained as intermediate products of the method of the invention for preparing of salts of weakly coordinating anions, corresponding to formula (4):

$$X(OR^F)_m \tag{4}$$

wherein X is selected from the group consisting of B, Al, Ga, In, P, As and Sb, m is 3 or 5 and $R^F$ is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups, perfluorinated groups being particularly preferred. By way of example, in formula (4), the following partially or completely fluorinated alkoxy radicals ($OR^F$) may again cited O—C(CF$_3$)$_3$, O—C(R$^1$)(CF$_3$)$_2$, O—C(R$^1$)(R$^2$)(CF$_3$) and O—C(R$^1$)(R$^2$)(R$^3$), wherein R$^1$, R$^2$ and R$^3$, independently in each case, are hydrogen, linear or branched, partially or completely fluorinated $C_1$ to $C_{20}$-alkyl groups, partially or completely fluorinated $C_6$ to $C_{20}$ aryl groups, and partially or completely fluorinated $C_3$ to $C_{10}$ cycloalkyl groups, provided that in the case of O—C(R$^1$)(R$^2$)(R$^3$) at least one of R$^1$, R$^2$ and R$^3$ is a partially or completely fluorinated radical as mentioned above.

Especially preferred are O—C(CF$_3$)$_3$ or an O—C(R$^1$)(R$^2$)(R$^3$) alkoxy radical as mentioned above, which have at least one R$^1$, R$^2$ and/or R$^3$ radical, which is a perfluorinated $C_1$ to $C_{10}$ alkyl group, and in particular a $C_1$ to $C_6$ alkyl group, such as for example —$C_6F_{13}$.

In a particularly preferred embodiment of the invention, in the alkoxy compounds of the element in formula (4), X is Al and $R^F$ is as defined above.

The invention is described further by the following, non-limiting examples.

EXAMPLES

Because of the sensitivity to hydrolysis and oxidation of AlMe$_3$, all work was carried out so as to exclude air and moisture, in appropriate apparatus and under an inert N$_2$ atmosphere with Schlenk and glove-box techniques. The glass apparatus was closed in part with stopcocks from J. YOUNG company or glass stoppers and was heated under an oil-pump vacuum before beginning the experiment. The solvent was dried by standard methods, distilled and degassed and stored under nitrogen over a molecular sieve (400 pm). To determine the amount of gas generated in the reaction, a water-filled, gauged glass tube was connected by tubing to the apparatus. The gas volume could be deduced from the displacement of the water.

NMR Spectra

NMR-spectra were recorded using CD$_2$Cl$_2$-solvent at 20° with a BRUKER AC spectrometer, with SiMe$_4$ ($^1$H, $^{13}$C) and AlCl$_3$($^{27}$Al) as references. The shifts are reported in ppm.
s=singlet, d=doublet, q=quartet, m=multiplet; j=coupling constant (hz)

HiResESI Spectra

HiResESI spectra were recorded using CD$_2$Cl$_2$-solvent at 200, using an IonSpec Ultima FT-ICR-MS.

In the following examples $R^F$ is (F$_3$C)$_3$C.

Example 1

Preparation of Aq[F—Al(OR$^F$)$_3$]

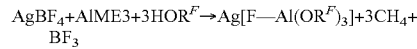

$$AgBF_4 + AlME_3 + 3HOR^F \xrightarrow{pentane} Ag[F—Al(OR^F)_3] + 3CH_4 + BF_3$$

In a 250 ml two-necked flask, which is fitted with a reflux condenser cooled by cryostat to −20° C., 1.40 ml (2.82 mol) AlMe$_3$ (dissolved in n-heptane, c=2.0 mol/l) is introduced into about 20 ml of pentane at 0° C.

Then 1.18 ml (8.47 mmol) of alcohol R$^F$OH is instilled with further stirring. After full methane formation (190 ml; 100%), 0.550 g (2.82 mmol) of solid light beige AgBF$_4$-salt is added at one time to the mixture of the already formed Al(OR$^F$)$_3$ using a Schlenk vessel. With stirring, the salt reacts with the Al(OR$^F$)$_3$, whereby a light beige residue forms. After the gas formation of BF$_3$ (31 ml; 100%), the solvent is removed under high vacuum at 0° C. A bright yellow powder remains, which is weighed. This corresponds to the desired product Ag[F—Al(OR$^F$)$_3$] (yield: 2.375 g; 98%).

TABLE 1

$^{13}$C- and $^{27}$Al-NMR Data for the Compound Ag[F—Al(OR$^F$)$_3$]

| compound/fragment | NMR-nucleus | δ [ppm] exp. |
|---|---|---|
| OC(CF$_3$)$_3$ | $^{13}$C | 119.3 q; $^1J_{CF}$ = 290.0 Hz |
| OC(CF$_3$)$_3$ | | 80.6 wide |
| [F—Al(OR$^F$)$_3$]$^-$ | $^{27}$Al | 41 d; $^1J_{AlF}$ = 67.6 Hz |

The HiResESI spectrum in CH$_2$Cl$_2$ confirms the theoretical mass of 751 for the anion [F—Al(OR$^F$)$_3$]$^-$.

Example 2

Preparation of [NBu$_4$] [F—Al(OR$^F$)$_3$]

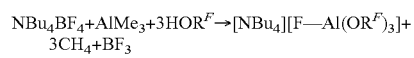

$$NBu_4BF_4 + AlMe_3 + 3HOR^F \xrightarrow{pentane} [NBu_4][F—Al(OR^F)_3] + 3CH_4 + BF_3$$

In a two-necked flask, which is fitted with a reflux condenser cooled by cryostat to −20° C., 1.40 ml (2.82 mol) of AlMe$_3$ (dissolved in n-heptane, c=2.0 mol/l) is introduced into about 20 ml of pentane. At 0° C., 1.18 ml (8.47 mmol) R$^F$OH is instilled with stirring and reflux. After full methane formation (190 ml; 100%), white Al(OR$^F$)$_3$ appears. After the addition of 0.929 g (2.82 mmol) of the white NBu$_4$BF$_4$-salt using a Schlenk apparatus, a bright residue forms with time, which precipitates. The formation of BF$_3$ gas is complete at 62 ml (100%). After removal of the solvent under high vacuum, a bright solid powder remains, which is constant in weight and corresponds to the product [(NBu$_4$][F—Al (OR$^F$)$_3$] (yield: 2.394 g; 85%).

TABLE 2

NMR Data for [(NBu$_4$][F—Al(OR$^F$)$_3$]

| compound/fragment | NMR-nucleus | δ [ppm] exp. |
|---|---|---|
| N (C$_4$H$_9$)$_4^+$ | $^1$H | 0.95 m + 1.37 m + 1.55 m + 3.05 m |
| OC(CF$_3$)$_3$ | $^{13}$C | 121.6 q; $^1J_{CF}$ = 291.6 Hz |
| OC(CF$_3$)$_3$ | | 79.9 wide |
| N(C$_4$H$_9$)$_4^+$ | | 13.2 s + 19.6 s + 23.9 s + 58.9 s |
| [F—Al(OR$^F$)$_3$]$^-$ | $^{27}$Al | 42 s |

The HiResESI spectrum clearly indicates the mass of the corresponding [F—Al(OR$^F$)$_3$]$^-$-anions at 751, which is analogous to the mass of anions in the silver salt compound Ag[F—Al(OR$^F$)$_3$] of Example 1.

Example 3

Preparation of Aq[(R$^F$O)$_3$Al—F—Al(OR$^F$)$_3$]

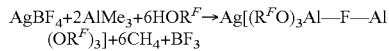

AgBF$_4$+2AlMe$_3$+6HOR$^F$→Ag[(R$^F$O)$_3$Al—F—Al(OR$^F$)$_3$]+6CH$_4$+BF$_3$

In a 250 ml two-necked flask, which is fitted with a reflux condenser cooled by cryostat to 20° C., 1.40 ml (2.82 mol) AlMe$_3$ (dissolved in n-heptane, c=2.0 mol/l) is introduced into about 20 ml pentane at 0° C. While adding 1.18 ml (8.47 mmol) of R$^F$OH, 190 ml (100%) of methane forms. After gas evolution is complete, white Al(OR$^F$)$_3$ forms.

The AgBF$_4$-salt (0.275 g; 1.412 mmol) is added to the mixture at one time using a Schlenk apparatus. At once, a viscous light beige solid material forms in a colorless supernatant solution. The volume of evolving BF$_3$ gas is complete (31 ml; 100%). After decanting the solvent under high pressure, a beige, large-grained powder remains, which is constant in weight and corresponds to the product Ag[(R$^F$O)$_3$Al—F—Al(OR$^F$)$_3$] (yield: 1.939 g; 86%).

TABLE 3

| NMR Data for Ag[(R$^F$O)$_3$Al—F—Al(OR$^F$)$_3$] | | |
|---|---|---|
| compound/fragment | NMR-nucleus | δ [ppm] exp. |
| OC(CF$_3$)$_3$ | $^{13}$C | 120.9 q; $^1J_{CF}$ = 291.1 Hz |
| OC(CF$_3$)$_3$ | | 79.9 broad |
| [(R$^F$O)$_3$Al—F—Al(OR$^F$)$_3$]$^-$ | $^{27}$Al | 34 s broad |

Example 4

Preparation of [NBu$_4$][R$^F$O)$_3$Al—F—Al(OR$^F$)$_3$]

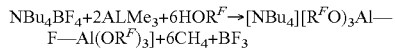

NBu$_4$BF$_4$+2ALMe$_3$+6HOR$^F$→[NBu$_4$][R$^F$O)$_3$Al—F—Al(OR$^F$)$_3$]+6CH$_4$+BF$_3$

In a 250 ml two-necked flask, which is fitted with a reflux condenser cooled by cryostat to –20° C., 1.40 ml (2.82 mol) of AlMe$_3$ (dissolved in n-heptane, c=2.0 mol/l) is introduced into about 20 ml pentane at 0° C. While adding 1.18 ml (8.47 mmol) of R$^F$OH, 190 ml (100%) of methane is formed After gas evolution is complete, white Al(OR$^F$)$_3$ forms.

The NBu$_4$BF$_4$-salt (0.464 g; 1.412 mmol) is added to the mixture at one time using a Schlenk apparatus. At once, a bright residue forms. The volume of evolving BF$_3$ gas is complete (31 ml; 100%). After decanting the solvent under high pressure, a colorless, slightly yellowish powder remains, which is constant in weight and corresponds to the product [NBu$_4$][(R$^F$O)$_3$Al—F—Al(OR$^F$)$_3$] (yield: 2.17 g; 89%).

TABLE 4

| NMR Data for [NBu$_4$][(R$^F$O)$_3$Al—F—Al(OR$^F$)$_3$] | | |
|---|---|---|
| compound/fragment | NMR-nucleus | δ [ppm] exp. |
| N(C$_4$H$_9$)$_4$$^+$ | $^1$H | 0.98 m + 1.37 m + 1.55 m + 3.01 m |
| OC(CF$_3$)$_3$ | $^{13}$C | 120.9 q; $^1J_{CF}$ = 291.2 Hz |
| OC(CF$_3$)$_3$ | | 80 broad |
| N(C$_4$H$_9$)$_4$$^+$ | | 13.2 s + 19.8 s + 24.0 s + 59.3 s |
| [(R$^F$O)$_3$Al—F—Al(OR$^F$)$_3$]$^-$ | $^{27}$Al | 34 s broad |

Example 5

Preparation of [NBu$_4$][(R$^F$O)$_3$Al—F—Al(OR$^F$)$_9$—F—Al(OR$^F$)$_3$]

In a two-necked flask, which is fitted with a reflux condenser cooled by cryostat to –20° C., 1.40 ml (2.82 mol) of AlMe$_3$ (dissolved in n-heptane, c=2.0 mol/l) is introduced into about 30 ml of heptane at 0° C. With further stirring, 1.18 ml (8.47 mmol) R$^F$OH is added dropwise. White Al(OR$^F$)$_3$ forms. After complete methane generation, 0.464 g (1.41 mmol) of white NBu$_4$BF$_4$-salt, dissolved in about 5 ml CH$_2$Cl$_2$, is added to the mixture at one time. A dark yellow solution forms, which contains a small amount of light beige precipitate. After complete generation of BF$_3$ gas (31 ml; 100%), stirring is continued for about one hour at 0° C. Then, the solution is refluxed for about 2 hours and the solvent is removed under high vacuum. A light beige oily-solid residue in the amount of 2.453 g remains, which crystallizes from CH$_2$Cl$_2$. This yields the product: [NBu$_4$][(R$^F$O)$_3$Al—F—Al(OR$^F$)$_2$—F—Al(OR$^F$)$_3$].

TABLE 5

| NMR Data for [NBu$_4$][(R$^F$O)$_3$Al—F—Al(OR$^F$)$_2$—F—Al(OR$^F$)$_3$] | | |
|---|---|---|
| compound/fragment | NMR-nucleus | δ [ppm] exp. |
| N(C$_4$H$_9$)$_4$$^+$ | $^1$H | 0.95 m + 1.36 m + .,49 m + 3.03 m |
| N(C$_4$H$_9$)$_4$$^+$ | $^{13}$C | 13.3 s + 19.9 s + 24.1 s + 59.4 s |
| OC(CF$_3$)$_3$ | | 120.9 q; $^1J_{CF}$ = 291.1 Hz[1)] |
| | | 121.9 q; $^1J_{CF}$ = 290.9 Hz[2)] |
| | | 120.8 q; $^1J_{CF}$ = 290.9 Hz[3)] |
| OC(CF$_3$)$_3$ | | 79.9 broad |
| [(R$^F$O)$_3$Al—F—Al(OR$^F$)$_2$—F—Al(OR$^F$)$_3$]$^-$ | $^{27}$Al | 35 s, very broad |

The invention claimed is:

1. A method for preparing salts of weakly coordinating anions of the type corresponding to the following formula (1), (2) or (3):

$$M[F\text{—}X(OR^F)_m]_z \qquad (1)$$

$$M[(^FRO)_mX\text{—}F\text{—}X(OR^F)_m]_z \qquad (2)$$

$$M[(^FRO)_mX\text{—}F\text{—}X(OR^F)_n\text{—}F\text{—}X(OR^F)_m]_z \qquad (3)$$

wherein, in a first step an organyl compound of an element $XR_m$ is reacted with a partially or completely fluorinated alcohol $^FROH$ in an organic, aprotic solvent and then, in a second step, the resulting alkoxy compound of the element $X(OR^F)_m$ is reacted with a suitable fluoride salt $M_yY_z$ so as to abstract a fluoride ion, if necessary under $XF_m$-catalysis, wherein X is selected from the group consisting of B, Al, Ga, In, P, As and Sb, M is a monovalent or bivalent cation, m is 3 or 5 and n is 2, if m is 3, and/or n is 4, if m is 5, y is 1 or 2, provided that, if y is 1, Y is a monovalent anion, or if y is 2, Y is a bivalent anion, and z is 1 or 2, provided that, if z is 1, M is a monovalent cation, or if z is 2, M is a bivalent cation.

2. The method according to claim 1 for the production of salts of weakly coordinating anions of the type corresponding to the following formula (1'), (2') or (3'):

$$M[F\text{—}Al(OR^F)_3]_z \qquad (1')$$

$$M[(^FRO)_3Al\text{—}F\text{—}Al(OR^F)_3]_z \qquad (2')$$

$$M[(^FRO)Al\text{—}F\text{—}Al(OR^F)\text{—}F\text{—}Al(OR^F)_3]_z \qquad (3')$$

wherein, in a first step an aluminum triorganyl compound $AlR_m$ is reacted with a partially or completely fluorinated alcohol $^FROH$ in an organic, aprotic solvent, and then, in a second step, the resulting aluminum trialkoxy compound $Al(OR^F)_3$ is reacted with a tetrafluoroborate salt $M(BF_4)_z$, if necessary, under $BF_3$-catalysis.

3. A method according to claim 1, wherein the aluminum trialkoxy compound $Al(OR^F)_3$ is reacted with the tetrafluoroborate salt $M(BF_4)_z$ at a ratio of 1:1, if z is 1, or is reacted at a ratio of 2:1, if z is 2.

4. A method according to claim 1, wherein the aluminum trialkoxy compound $Al(OR^F)_3$ is reacted with the tetrafluoroborate salt $M(BF_4)_z$ at a ratio of 2:1, if z is 1, or is reacted at a ratio of 4:1, if z is 2.

5. A method according to claim 1, wherein the organic, aprotic solvent is selected from the group consisting of pentane, hexane, heptane, octane, benzene, toluene, cresol, chlorobenzene and trichlorobenzene.

6. A method according to claim 1, wherein R is a radical selected from the group consisting of hydrogen, methyl, ethyl, n-propyl, i-propyl, n-butyl, i-butyl, t-butyl, phenyl and tolyl.

7. A method according to claim 1, wherein $R^F$ is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups.

8. A method according to claim 1, wherein, if z is 1, M is selected from the group consisting of alkali metal ions, $In^+$, $Ti^+$, $Ag^+$, $Cu^+$, $NR'_4{}^+$, $PR'_4{}^+$, wherein R' is, independently in each case, hydrogen, a linear or branched $C_1$ to $C_{20}$-alkyl radical or substituted or unsubstituted aryl radical, and imidazolium, or, if z is 2, M is selected from the group consisting of $Ni^{2+}$, $Cu^{2+}$, $Zn^{2+}$, $Pd^{2+}$, $Rh^{2+}$, and $Pt^{2+}$.

9. A method according to claim 1, wherein, in a first step, the aluminum triorganyl compound $AlMe_3$ is reacted with a partially or completely fluorinated alcohol $^FROH$ in pentane at a ratio of 1:3 and then, in a second step, the resulting aluminum trialkoxy compound $Al(OR^F)_3$ is reacted with tetrafluoroborate salt $M(BF_4)_z$ at a ratio of 1:1, if z is 1, or at a ratio of 2:1, if z is 2, to yield a compound corresponding to formula (1') above.

10. A method according to claim 1, wherein, in a first step, the aluminum triorganyl compound $AlMe_3$ is reacted with a partially or completely fluorinated alcohol $^FROH$ in pentane at a ratio of 1:3 and, then in a second step, the resulting aluminum trialkoxy compound $Al(OR^F)_3$ is reacted with tetrafluoroborate salt $M(BF_4)_z$ at a ratio of 2:1, if z is 1, or at a ratio of 4:1, if z is 2, to yield a compound corresponding to formula (2') above.

11. A method according to claim 1, wherein, in a first step, the aluminum triorganyl compound $AlMe_3$ is reacted with a partially or completely fluorinated alcohol $^FROH$ in heptane at a ratio of 1:3 and then, in a second step, the resulting aluminum trialkoxy compound $Al(OR^F)_3$ is reacted with tetrafluoroborate salt $M(BF_4)_z$ at a ratio of 2:1 if z is 1, or at a ratio of 4:1, if z is 2, to yield a compound corresponding to formula (3') above.

12. A method according to claim 9, wherein M is $Ag^+$ or $NBu_4{}^+$ and $R^F$ is $(F_3C)_3C$.

13. A method according to claim 10 wherein M is $Ag^+$ or $NBu_4{}^+$ and $R^F$ is $(F_3C)_3C$.

14. Salts of weakly coordinating anions corresponding to formula (3):

$$M[(^FRO)_mX\text{—}F\text{—}X(OR^F)_n\text{—}F\text{—}X(OR^F)_m]_z \qquad (3)$$

wherein X is selected from the group consisting of B, Al, Ga, In, P, As and Sb,

M is a monovalent or bivalent cation, m is 3 or 5 and n is 2, if m is 3, and/or n is 4, if m is 5, z is 1 or 2, provided that, if z is 1, M is a monovalent anion, and/or if z is 2, M is a bivalent anion, and wherein, if z is 1, M is selected from the group consisting of alkali metal ions, $In^+$, $Ti^+$, $Ag^+$, $Cu^+$, $NR'_4{}^+$, $PR'_4{}^+$, wherein R' is, independently in each case, hydrogen, a linear or branched $C_1$ to $C_{20}$-alkyl radical or substituted or unsubstituted aryl radical, and imidazolium, or, if z is 2, M is selected from the group consisting of $Ni^{2+}$, $Cu^{2+}$, $Zn^{2+}$, $Pd^{2+}$, $Rh^{2+}$, and $Pt^{2+}$, and $R^F$ is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups.

15. The salts of weakly coordinating anions according to claim 14, represented by the formula (3'):

$$M[(^FRO)_3Al\text{—}F\text{—}Al(OR^F)_2\text{—}F\text{—}Al(OR^F)_3]_z \qquad (3')$$

wherein z, M and $R^F$ are as defined above.

16. The salts according to claim 14, wherein M is $Ag^+$ or $NBu_4{}^+$ and $R^F$ is $(F_3C)_3C$.

17. An alkoxy compound of an element, represented by formula (4):

$$X(OR^F)_m \qquad (4)$$

wherein X is selected from the group consisting of B, Al, Ga, In, P, As and Sb, m is 3 or 5 and $R^F$ is selected from the group consisting of linear or branched, partially or completely fluorinated $C_1$ to $C_{10}$ alkyl groups, partially or completely fluorinated $C_6$ to $C_{20}$ aryl groups, and partially or completely fluorinated $C_3$ to $C_{10}$ cycloalkyl groups.

18. The alkoxy compound of an element according to claim 17, wherein X is Al.

19. A method according to claim 11 wherein M is $Ag^+$ or $NBu_4^+$ and $R^F$ is $(F_3C)_3C$.

* * * * *